United States Patent
Boileau et al.

(10) Patent No.: US 7,613,508 B2
(45) Date of Patent: Nov. 3, 2009

(54) IMPLANTABLE CARDIAC STIMULATION DEVICE, SYSTEM AND METHOD WHICH PROVIDES AN ELECTROGRAM SIGNAL FACILITATING MEASUREMENT OF SLOW-CHANGING ELECTROGRAM FEATURES

(75) Inventors: Peter Boileau, Valencia, CA (US); Gene A. Bornzin, Simi Valley, CA (US); Jong Gill, Valencia, CA (US)

(73) Assignee: Pacesetter, Inc., Sylmar, CA (US)

( * ) Notice: Subject to any disclaimer, the term of this patent is extended or adjusted under 35 U.S.C. 154(b) by 81 days.

(21) Appl. No.: 11/871,873

(22) Filed: Oct. 12, 2007

(65) Prior Publication Data
US 2008/0033499 A1 Feb. 7, 2008

Related U.S. Application Data

(63) Continuation-in-part of application No. 10/723,027, filed on Nov. 25, 2003, now Pat. No. 7,289,848, which is a continuation of application No. 09/963,207, filed on Sep. 25, 2001, now Pat. No. 6,658,283.

(51) Int. Cl.
*A61B 5/042* (2006.01)
(52) U.S. Cl. ...................................... 600/509
(58) Field of Classification Search ............... 607/4–28; 600/508–522
See application file for complete search history.

(56) References Cited

U.S. PATENT DOCUMENTS

| | | | |
|---|---|---|---|
| 5,324,310 A | 6/1994 | Greeninger et al. | |
| 5,448,997 A | 9/1995 | Kruse et al. | |
| 5,466,254 A | 11/1995 | Helland | |
| 5,542,430 A | 8/1996 | Farrugia et al. | |
| 5,605,158 A | 2/1997 | Snell | |
| 5,740,811 A | 4/1998 | Hedberg et al. | |
| 5,954,666 A | 9/1999 | Snell | |
| 6,249,705 B1 | 6/2001 | Snell | |
| 6,317,625 B1 | 11/2001 | Olson et al. | |
| 7,349,732 B1 * | 3/2008 | Kil et al. ..................... 600/510 |
| 2002/0123770 A1 | 9/2002 | Combs et al. | |

OTHER PUBLICATIONS

Medtronic Reveal® Plus Insertable Loop Recorder Brochure; pp. 1-10; publication date unknown.
Medtronic Reveal® Plus Insertable Loop Recorder Implant & Programming Guide; pp. 1-35; publication date unknown.
NonFinal Office Action, mailed Mar. 24, 2003: Grandparent U.S. Appl. No. 09/963,207.
Notice of Allowance, mailed Jul. 21, 2003: Grandparent U.S. Appl. No. 09/963,207.
NonFinal Office Action, mailed Apr. 19, 2006: Parent U.S. Appl. No. 10/723,027
Notice of Allowance, mailed Jun. 29, 2007: Parent U.S. Appl. No. 10/723,027.

* cited by examiner

*Primary Examiner*—Scott M Getzow

(57) ABSTRACT

An implantable cardiac system including an implantable cardiac stimulation device provides a heart activity signal of a heart facilitating measurement of slowly changing electrogram features. The system comprises at least one implantable electrode arrangement that senses cardiac electrical activity and provides an intracardiac electrogram signal, a first high pass filter that filters the electrogram and an equalizer that filters the filtered electrogram signal. The equalizer has a transfer function that is non-decreasing for frequencies up to a lower frequency breakpoint that is less than the upper frequency breakpoint, decreasing for frequencies between the lower frequency breakpoint and the upper frequency breakpoint, and generally flat for frequencies above the upper frequency breakpoint through a bandpass region of interest.

16 Claims, 9 Drawing Sheets

FIG. 4

| SEL 0 | SEL 1 | SEL 2 | ATRIAL ELECTRODE CONFIGURATION |
|---|---|---|---|
| 0 | 0 | 0 | $A_R$ TIP TO $V_R$ RING |
| 0 | 0 | 1 | $A_R$ TIP TO CASE |
| 0 | 1 | 0 | $A_R$ TIP TO $V_R$ RING |
| 0 | 1 | 1 | $A_R$ TIP TO $A_R$ RING |
| 1 | 0 | 0 | $A_R$ RING TO $V_R$ RING |
| 1 | 0 | 1 | $A_R$ RING TO CASE |
| 1 | 1 | 0 | $A_R$ RING TO $V_R$ TIP |
| 1 | 1 | 1 | $A_R$ RING TO $V_R$ RING |

FIG. 5

| SEL 0 | SEL 1 | SEL 2 | VENTRICULAR ELECTRODE CONFIGURATION |
|---|---|---|---|
| 0 | 0 | 0 | $V_R$ TIP TO $A_R$ RING |
| 0 | 0 | 1 | $V_R$ TIP TO CASE |
| 0 | 1 | 0 | $V_R$ TIP TO $A_R$ RING |
| 0 | 1 | 1 | $V_R$ TIP TO $V_R$ RING |
| 1 | 0 | 0 | $V_R$ RING TO $A_R$ RING |
| 1 | 0 | 1 | $V_R$ RING TO CASE |
| 1 | 1 | 0 | $V_R$ RING TO $A_R$ TIP |
| 1 | 1 | 1 | $V_R$ RING TO $V_R$ RING |

IMPLANTABLE CARDIAC STIMULATION DEVICE, SYSTEM AND METHOD WHICH PROVIDES AN ELECTROGRAM SIGNAL FACILITATING MEASUREMENT OF SLOW-CHANGING ELECTROGRAM FEATURES

CROSS-REFERENCE TO RELATED APPLICATIONS

The present application is a continuation-in-part of U.S. patent application Ser. No. 10/723,027 filed Nov. 25, 2003, which is a continuation of U.S. patent application Ser. No. 09/963,207, filed Sep. 25, 2001, entitled "Implantable Cardiac Stimulation Device, System and Method Which Provides an Electrogram Signal Having the Appearance of a Surface Electrogram," now U.S. Pat. No. 6,658,283, issued on Dec. 2, 2003.

FIELD OF THE INVENTION

The present invention generally relates to an implantable cardiac device. The present invention more particularly relates to an implantable cardiac stimulation device, system, and method which processes electro gram signals to support measurement of slowly changing electro gram features.

BACKGROUND OF THE INVENTION

Implantable cardiac devices are well known in the art. They may take the form of implantable defibrillators or cardioverters which treat accelerated rhythms of the heart such as fibrillation or implantable pacemakers which maintain the heart rate above a prescribed limit, such as, for example, to treat a bradycardia. Implantable cardiac devices are also known which incorporate both a pacemaker and a defibrillator (ICD).

A pacemaker may be considered as having two major components. One component is a pulse generator which generates the pacing stimulation pulses and includes the electronic circuitry and the power cell or battery. The other component is the lead, or leads, which electrically couple the pacemaker to the heart.

Pacemakers deliver pacing pulses to the heart to cause the stimulated heart chamber to contract when the patient's own intrinsic rhythm fails. To this end, pacemakers include sensing circuits that sense cardiac activity for the detection of intrinsic cardiac events such as intrinsic atrial events (P waves) and intrinsic ventricular events (R waves). By monitoring such P waves and/or R waves, the pacemaker circuits are able to determine the intrinsic rhythm of the heart and provide stimulation pacing pulses that force atrial and/or ventricular depolarizations at appropriate times in the cardiac cycle when required to help stabilize the electrical rhythm of the heart.

Pacemakers are described as single-chamber or dual-chamber systems. A single-chamber system stimulates and senses the same chamber of the heart (atrium or ventricle). A dual-chamber system stimulates and/or senses in both chambers of the heart (atrium and ventricle). Dual-chamber systems may typically be programmed to operate in either a dual-chamber mode or a single-chamber mode.

Implantable cardiac stimulation devices conventionally include an internal telemetry circuit permitting the devices to communicate with an external programmer. The external programmers also include a telemetry circuit with an external antenna or "wand" which is held over the implant site to allow the communication between the programmer and the implanted device. With the communication channel thus established, the programmer permits the attending medical personnel to set device operating modes and stimulation and sensing parameters within the device. The communication channel also permits the device to convey to the external programmer operating and sensed physiological data for display. The physiological data may include an intracardiac electrogram (IEGM). The IEGM may be prestored in the device and conveyed to the programmer responsive to a suitable external command from the programmer. The IEGMs are typically stored in response to high rate ventricular events or high rate atrial event triggers. The result is that physicians have more insight into the operation of the devices and have more information about the underlying rhythm that interacts with the device.

In addition to the IEGMs, physicians would like to be provided with a surface electrocardiogram (EKG). Their desire is based upon their day-to-day use of surface EKGs to make diagnosis of arrhythmias. Hence, with both IEGMs and surface EKGs, physicians will have more confidence that they will be able to discern exactly the underlying arrhythmic event that triggered the IEGM storage.

Unfortunately, implantable devices cannot provide surface EKGs. While some programmers of implantable cardiac stimulation systems do accommodate the display of surface EKGs, the surface EKGs available are taken at regular follow-up visits and thus after the arrhythmic event and IEGM storage have occurred. An after the fact surface EKG is not very helpful in support of a diagnosis of a prior arrhythmic episode.

Surface EKGs are particularly advantageous because they contain low frequency components suitable for measuring slowly changing EKG features. One such feature of preferred measure is the ST segment elevation. Measurement of ST segment elevation is very useful in diagnosing myocardial ischemia.

Myocardial ischemia results from insufficient blood flow to the heart muscle. Ischemia may occur chronically to varying degrees due to coronary artery disease (CAD) or acutely due to sudden increased demand, embolism or vasospasm. Ischemia can lead to angina and eventually to myocardial infarction resulting in permanent damage to the heart muscle. Both ischemia and infarction can trigger fatal arrhythmias.

In patients who have angina as a symptom of coronary artery disease, three to four episodes of silent ischemia (ischemia without angina) occur for every symptomatic episode. Objective evidence of ischemia, even when asymptomatic, is associated with negative clinical outcomes.

Ischemia can be detected by electrocardiographic changes. The classic electrocardiographic feature associated with myocardial ischemia (MI) is a change in the amplitude of the ST segment relative to the isoelectric baseline. Usually, a diagnostic 12-lead EKG is used. Detection through surface EKG is done only briefly and infrequently in the clinic or through the use of a holter monitor. Only those ischemic events which happen to occur, or which may be provoked by stress tests during monitoring are detected. The nature of electrocardiographic changes and the leads on which they appear are used to localize the region of ischemia.

A long-term record of ischemia burden obtained through continuous monitoring would be very useful as an adjunct to current methods of ischemia detection and diagnosis. Such a record may reveal infrequent or unprovokable ischemia, perhaps associated with nascent CAD, vasospasm or embolism. Such a record could reveal trends in the progression or regression of CAD. It could also be used to gauge the efficacy of, and/or patient compliance with, a course of medication.

Implantable medical devices (IMDs) such as pacemakers and ICDs offer an ideal platform for ischemia burden monitoring. IMDs can constantly monitor the electrophysiological conditions of patients and detect the onset and/or the burden of ischemia based on ST level change detected from IEGMs of implanted lead electrodes. Other applications may include alerting the patient of an ischemic episode which may not otherwise produce symptoms (silent MI), remotely notifying a physician or monitoring center upon MI detection, and releasing antithrombotic or thrombolytic medication upon MI detection.

A particular challenge exists for detection of MI via changes to the ST segment using pacemakers and ICDs. The challenge is that the ST segment is a slow-changing feature of the electrogram (voltage vs. time). Therefore, it would be required that the signal path of the IMD faithfully transmit low-frequency information if the ST segment is to be used for detection of MI. Pacemakers and defibrillators typically attenuate electrogram frequencies below 1 Hz. By comparison, the standard diagnostic ECG high pass filter cutoff frequency is 0.05 Hz. That is, frequency components are faithfully reproduced all the way down to 0.05 Hz.

Unfortunately, much of the useful information in the ST segment is carried by frequency components between 0.05 Hz and 1 Hz. Investigations have demonstrated that high pass filtering IEGMs with a 1 Hz cutoff significantly negatively impacts (compared to a 0.05 Hz cutoff frequency) the ability of MI detection algorithms to extract information from the ST segment useful to the task of MI detection. If the high-pass filter cutoff frequency were 0.25 Hz or lower, most of the ability of MI detection algorithms to effectively detect MI would be preserved.

One solution is to change the hardware of pacemakers or defibrillators to lower the high pass frequency cutoff. However, this solution by itself has potential negative effects. The high pass cutoff frequency of 1 Hz was chosen in pacemakers and ICDs for many good reasons. For example, the 1 Hz cutoff removes much of the respiration artifact from the IEGM. It also attenuates motion artifact. It also attenuates the unavoidable slow-changing voltage due to the slow recharge phase after a pacing pulse. This slow-recharge signal could be very large with high-polarizing leads.

If the IEGM channel high pass cutoff frequency is decreased, these formerly attenuated slow-changing signals will become larger relative to signals of interest, e.g. R-waves and T-waves. If they become large enough, there will be no way to prevent IEGM signals from being clipped prior to being digitized while still preserving sufficient resolution of the signals of interest. If clipping occurs, information is irretrievably lost and the usefulness of the IEGM channel is severely compromised or lost altogether unless the cutoff frequency change is performed by additional signal processing separate from the normal signal processing.

The measurement of slow-changing features of individual QRST complexes may be desirable for other purposes. For example, features of ST segment and T-wave morphology may be used to monitor blood glucose level or cardioactive drug action. Other slow-changing electrogram features include P-R segment elevation.

For measuring slow-changing EGM features, designing the pacemaker and ICD front end circuitry to lower the high-pass cutoff frequency would be ideal, as a high signal-to-noise ratio would be preserved throughout the signal path for all frequencies of interest. However such a design could have overall negative system impacts, foreseen and unforeseen. It would thus be desirable if the hardware front end could remain unchanged and IEGMs post-processed only as needed for ischemia detection or other purposes, thus eliminating the risks associated with such a hardware design.

SUMMARY OF THE INVENTION

The invention provides an implantable cardiac system including an implantable cardiac stimulation device that provides a heart activity signal of a heart facilitating measurement of slowly changing electrogram features. The system comprises at least one implantable electrode arrangement that senses cardiac electrical activity and provides an intracardiac electrogram signal, a first high-pass filter with a cutoff frequency at an upper frequency breakpoint that filters the intracardiac electrogram signal, and an equalizer that filters the filtered intracardiac electrogram signal. The equalizer has a transfer function derived by multiplying a reciprocal of the transfer function of the first high pass filter by a transfer function of a second high pass filter with a cutoff frequency at a lower frequency breakpoint. The transfer function of the equalizer is non-decreasing for frequencies up to the lower frequency breakpoint.

The transfer function of the equalizer may increase for frequencies up to the lower frequency breakpoint. The transfer function of the equalizer may have a second order response from the lower frequency breakpoint to the upper frequency breakpoint. The upper frequency breakpoint may be on the order of 1 Hertz. The lower frequency breakpoint may be less than about 0.25 Hertz.

The electrode arrangement may include an electrode adapted for implant in the right atrium of the heart or proximate to a ventricle of the heart. The electrode arrangement may comprise a first electrode adapted for implant in, on or proximate to an atrium of the heart and a second electrode adapted for implant in, on or proximate to a ventricle of the heart.

The invention further provides a method of providing a heart activity signal of a heart which facilitates measurement of slowly changing electrogram features. The method comprises sensing cardiac electrical activity with at least one implanted electrode arrangement to provide an electrogram signal and filtering the electrogram signal with a first high-pass filter with a cutoff frequency at an upper frequency breakpoint. The method further includes filtering the filtered electrogram signal with a equalizer having a transfer function that is: non-decreasing for frequencies up to a lower frequency breakpoint that is less than the upper frequency breakpoint, decreasing for frequencies between the lower frequency breakpoint and the upper frequency breakpoint, and generally flat for frequencies above the upper frequency breakpoint through a bandpass region of interest.

The invention still further provides an implantable cardiac system including an implantable cardiac stimulation device that provides a heart activity signal of a heart facilitating measurement of slowly changing electrogram features. The system comprises at least one implantable electrode arrangement that senses cardiac electrical activity and provides an electrogram signal, a first high-pass filter with a cutoff frequency at an upper frequency breakpoint that filters the electrogram signal, and a plurality of serially arranged equalizers that filter the filtered electrogram signal, each equalizer having a transfer function derived as a function of a reciprocal transfer function of the first high pass filter and a transfer function of a second high pass filter with a cutoff frequency at a lower frequency breakpoint.

BRIEF DESCRIPTION OF THE DRAWINGS

Further features and advantages of the present invention may be more readily understood by reference to the following description taken in conjunction with the accompanying drawings, in which:

FIG. 4 is a chart illustrating the manner in which a first sensing IEGM electrode configuration may be selected from a plurality of possible sensing electrode configurations;

FIG. 5 is a chart illustrating the manner in which a second sensing IEGM electrode configuration may be selected from a second plurality of possible sensing electrode configurations;

DETAILED DESCRIPTION OF THE PREFERRED EMBODIMENTS

The following description is of the best mode presently contemplated for practicing the invention. This description is not to be taken in a limiting sense but is made merely for the purpose of describing the general principles of the invention. The scope of the invention should be ascertained with reference to the issued claims. In the description of the invention that follows, like numerals or reference designators will be used to refer to like parts or elements throughout.

Figure 1:
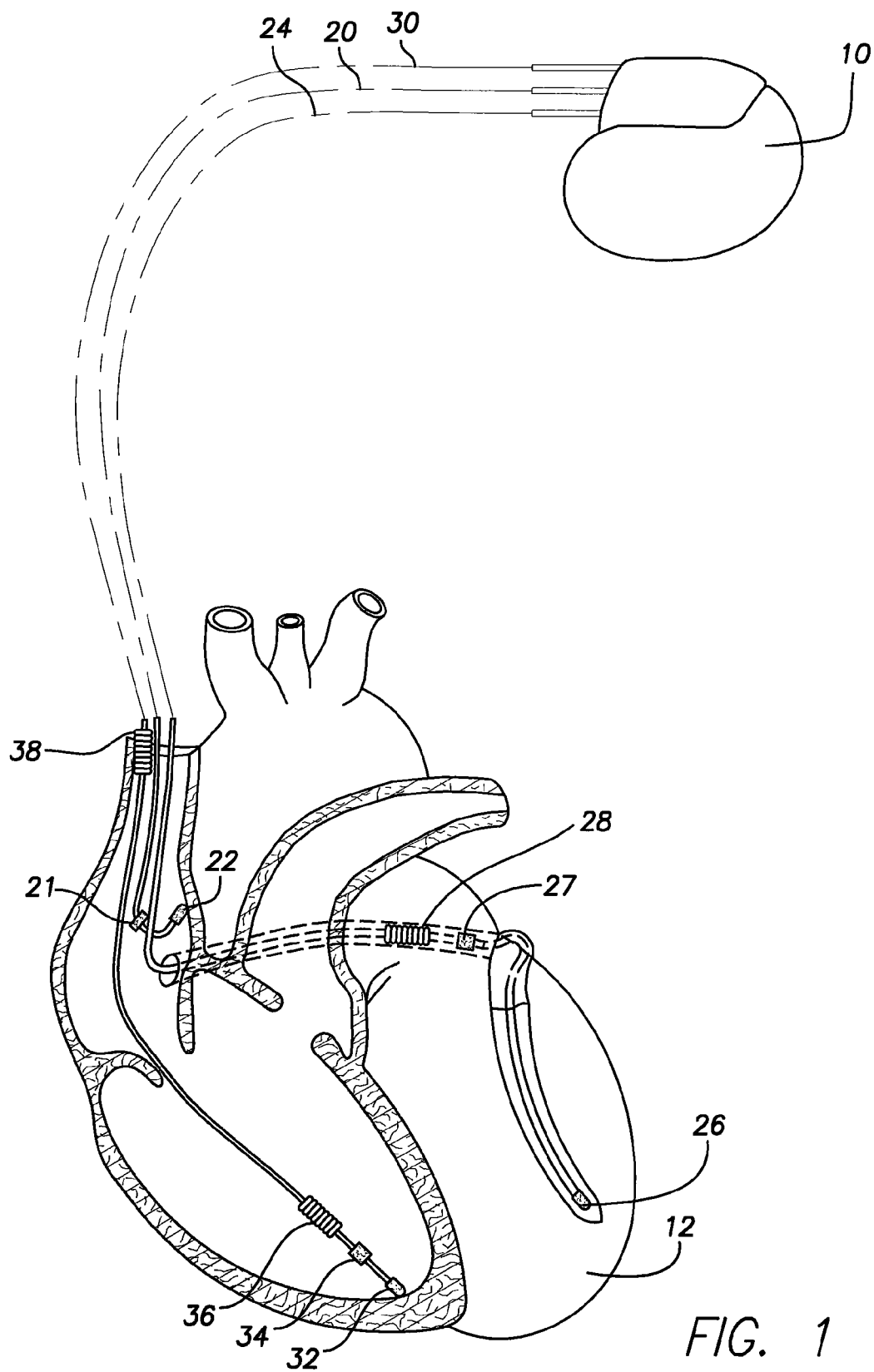
FIG. 1 is a simplified diagram illustrating an implantable stimulation device and lead system for delivering multi-chamber stimulation and shock therapy.

As shown in FIG. 1, there is a stimulation device 10 in electrical communication with a patient's heart 12 by way of three leads, 20, 24 and 30, suitable for delivering multi-chamber stimulation and shock therapy. To sense atrial cardiac signals and to provide right atrial chamber stimulation therapy, the stimulation device 10 is coupled to an implantable right atrial lead 20 having at least an atrial tip electrode 22, which typically is implanted in the patient's right atrial appendage. The right atrial lead 20 may further include a right atrial ring electrode 21 to permit unipolar sensing with that electrode or bipolar sensing with the right atrial tip electrode 22.

To sense left atrial and ventricular cardiac signals and to provide left chamber pacing therapy, the stimulation device 10 is coupled to a "coronary sinus" lead 24 designed for placement in the "coronary sinus region" via the coronary sinus os for positioning a distal electrode adjacent to the left ventricle and/or additional electrode(s) adjacent to the left atrium. As used herein, the phrase "coronary sinus region" refers to the vasculature of the left ventricle, including any portion of the coronary sinus, great cardiac vein, left marginal vein, left posterior ventricular vein, middle cardiac vein, and/or small cardiac vein or any other cardiac vein accessible by the coronary sinus.

Accordingly, an exemplary coronary sinus lead 24 is designed to receive atrial and ventricular cardiac signals and to deliver left ventricular pacing therapy using at least a left ventricular tip electrode 26, left atrial pacing therapy using at least a left atrial ring electrode 27, and shocking therapy using at least a left atrial coil electrode 28. For a complete description of a coronary sinus lead, see U.S. Pat. No. 5,466,254, "Coronary Sinus Lead with Atrial Sensing Capability" (Helland), which patent is hereby incorporated herein by reference.

The stimulation device 10 is also shown in electrical communication with the patient's heart 12 by way of an implantable right ventricular lead 30 having, in this embodiment, a right ventricular tip electrode 32, a right ventricular ring electrode 34, a right ventricular (RV) coil electrode 36, and an SVC coil electrode 38. Typically, the right ventricular lead 30 is transvenously inserted into the heart 12 so as to place the right ventricular tip electrode 32 in the right ventricular apex so that the RV coil electrode will be positioned in the right ventricle and the SVC coil electrode 38 will be positioned in the superior vena cava. Accordingly, the right ventricular lead 30 is capable of receiving cardiac signals, and delivering stimulation in the form of pacing and shock therapy to the right ventricle.

Figure 2:
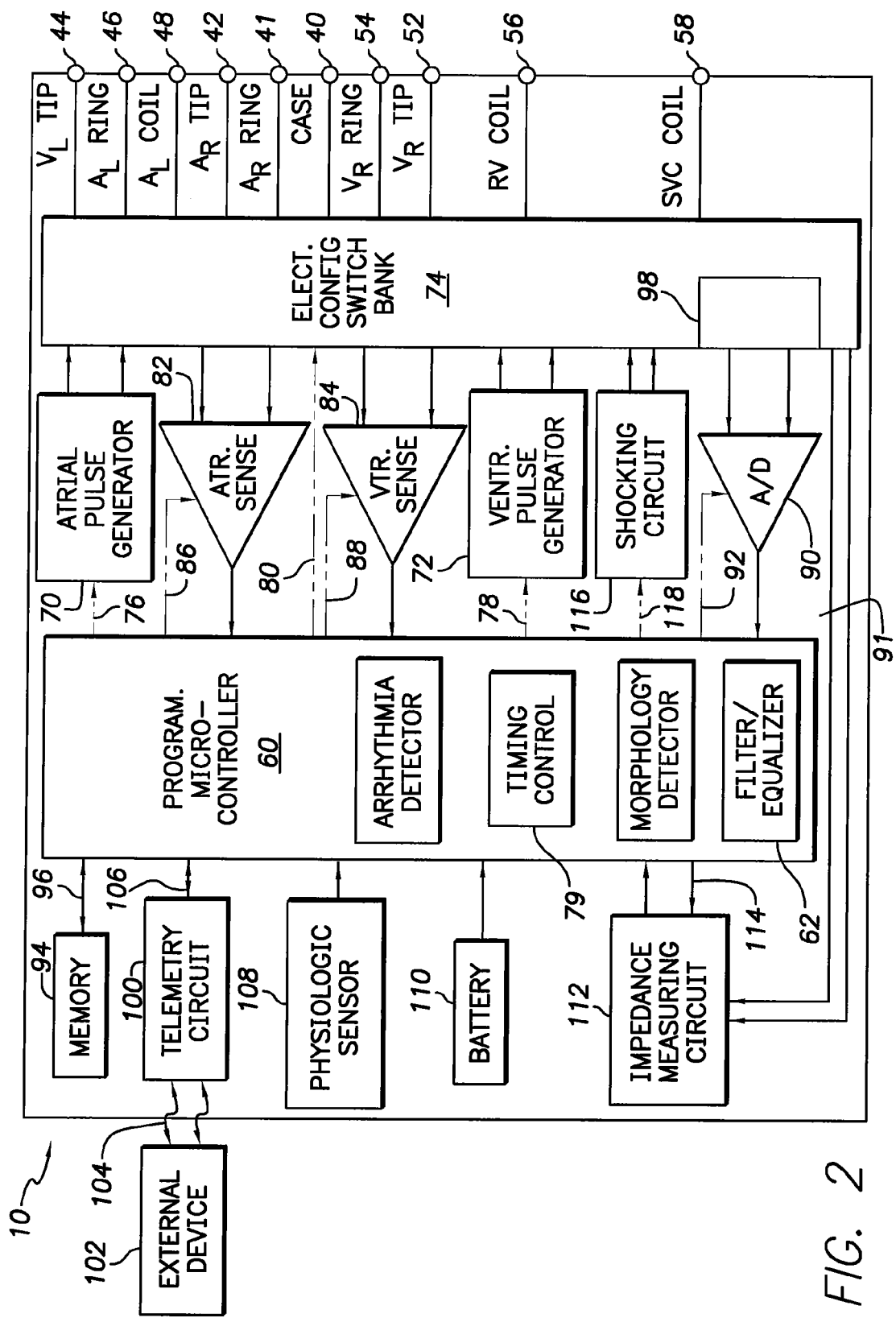
FIG. 2 is a functional block diagram of a multi-chamber implantable stimulation device illustrating the basic elements of a stimulation device which can provide cardioversion, defibrillation and pacing stimulation in four chambers of the heart as well as a processed IEGM signal or an IEGM signal to be processed for providing a heart activity signal resembling a surface EKG.

As illustrated in FIG. 2, a simplified block diagram is shown of the multi-chamber implantable stimulation device 10, which is capable of treating both fast and slow arrhythmias with stimulation therapy, including cardioversion, defibrillation, and pacing stimulation. While a particular multi-chamber device is shown, this is for illustration purposes only, and one of skill in the art could readily duplicate, eliminate or disable the appropriate circuitry in any desired combination to provide a device capable of treating the appropriate chamber(s) with cardioversion, defibrillation and pacing stimulation.

The housing 40 for the stimulation device 10, shown schematically in FIG. 2, is often referred to as the "can", "case" or "case electrode" and may be programmably selected to act as the return electrode for all "unipolar" modes. The housing 40 may further be used as a return electrode alone or in combination with one or more of the coil electrodes, 28, 36 and 38, for shocking purposes. The housing 40 further includes a connector (not shown) having a plurality of terminals, 41, 42, 44, 46, 48, 52, 54, 56, and 58 (shown schematically and, for convenience, the names of the electrodes to which they are connected are shown next to the terminals). As such, to achieve right atrial sensing and pacing, the connector includes at least a right atrial tip terminal ($A_R$ TIP) 42 adapted for connection to the atrial tip electrode 22 and a right atrial ring terminal ($A_R$ RING) 41 adapted for connection to the atrial ring electrode 21.

To achieve left chamber sensing, pacing and shocking, the connector includes at least a left ventricular tip terminal ($V_L$ TIP) 44, a left atrial ring terminal ($A_L$ RING) 46, and a left atrial shocking terminal ($A_L$ COIL) 48, which are adapted for connection to the left ventricular ring electrode 26, the left atrial ring electrode 27, and the left atrial coil electrode 28, respectively.

To support right chamber sensing, pacing and shocking, the connector further includes a right ventricular tip terminal ($V_R$ TIP) 52, a right ventricular ring terminal ($V_R$ RING) 54, a right ventricular shocking terminal ($R_V$ COIL) 56, and an SVC shocking terminal (SVC COIL) 58, which are adapted for connection to the right ventricular tip electrode 32, right ventricular ring electrode 34, the RV coil electrode 36, and the SVC coil electrode 38, respectively.

At the core of the stimulation device 10 is a programmable microcontroller 60 which controls the various modes of stimulation therapy. As is well known in the art, the microcontroller 60 typically includes a microprocessor, or equivalent control circuitry, designed specifically for controlling the delivery of stimulation therapy and may further include RAM or ROM memory, logic and timing circuitry, state machine circuitry, and I/O circuitry. Typically, the microcontroller 60 includes the ability to process or monitor input signals (data) as controlled by a program code stored in a designated block of memory. The details of the design and operation of the microcontroller 60 are not critical to the present invention. Rather, any suitable microcontroller 60 may be used that carries out the functions described herein. The use of microprocessor-based control circuits for performing timing and data analysis functions are well known in the art.

As shown in FIG. 2, an atrial pulse generator 70 and a ventricular pulse generator 72 generate pacing stimulation pulses for delivery by the right atrial lead 20, the right ventricular lead 30, and/or the coronary sinus lead 24 via an electrode configuration switch 74. It is understood that in order to provide stimulation therapy in each of the four chambers of the heart, the atrial and ventricular pulse generators, 70 and 72, may include dedicated, independent pulse generators, multiplexed pulse generators, or shared pulse generators. The pulse generators, 70 and 72, are controlled by the microcontroller 60 via appropriate control signals, 76 and 78, respectively, to trigger or inhibit the stimulation pulses.

The microcontroller 60 further includes timing control circuitry 79 which is used to control the timing of such stimulation pulses (e.g., pacing rate, atrio-ventricular (AV) delay, atrial interconduction (A-A) delay, or ventricular interconduction (V-V) delay, etc.) as well as to keep track of the timing of refractory periods, blanking intervals, noise detection windows, evoked response windows, alert intervals, marker channel timing, etc., which is well known in the art.

The switch 74 includes a plurality of switches for connecting the desired electrodes to the appropriate I/O circuits, thereby providing complete electrode programmability. Accordingly, the switch 74, in response to a control signal 80 from the microcontroller 60, determines the polarity of the stimulation pulses (e.g., unipolar, bipolar, combipolar, etc.) by selectively closing the appropriate combination of switches (not shown) as is known in the art.

Atrial sensing circuits 82 and ventricular sensing circuits 84 may also be selectively coupled to the right atrial lead 20, coronary sinus lead 24, and the right ventricular lead 30, through the switch 74 for detecting the presence of cardiac activity in each of the four chambers of the heart. Accordingly, the atrial (ATR. SENSE) and ventricular (VTR. SENSE) sensing circuits, 82 and 84, may include dedicated sense amplifiers, multiplexed amplifiers, or shared amplifiers. The switch 74 determines the "sensing polarity" of the cardiac signal by selectively closing the appropriate switches, as is also known in the art. In this way, the clinician may program the sensing polarity independent of the stimulation polarity.

Each sensing circuit, 82 and 84, preferably employs one or more low power, precision amplifiers with programmable gain and/or automatic gain control, bandpass filtering, and a threshold detection circuit, as known in the art, to selectively sense the cardiac signal of interest. The automatic gain control enables the device 10 to deal effectively with the difficult problem of sensing the low amplitude signal characteristics of atrial or ventricular fibrillation. The outputs of the atrial and ventricular sensing circuits, 82 and 84, are connected to the microcontroller 60 which, in turn, are able to trigger or inhibit the atrial and ventricular pulse generators, 70 and 72, respectively, in a demand fashion in response to the absence or presence of cardiac activity in the appropriate chambers of the heart. The sensing circuits, 82 and 84, in turn, receive control signals over signal lines, 86 and 88, from the microcontroller 60 for purposes of controlling the gain, threshold, polarization charge removal circuitry (not shown), and the timing of any blocking circuitry (not shown) coupled to the inputs of the sensing circuits, 82 and 86, as is known in the art.

For arrhythmia detection, the device 10 utilizes the atrial and ventricular sensing circuits, 82 and 84, to sense cardiac signals to determine whether a rhythm is physiologic or pathologic. As used herein "sensing" is reserved for the noting of an electrical signal, and "detection" is the processing of these sensed signals and noting the presence of an arrhythmia. The timing intervals between sensed events (e.g., P-waves, R-waves, and depolarization signals associated with fibrillation which are sometimes referred to as "F-waves" or "Fib-waves") are then classified by the microcontroller 60 by comparing them to a predefined rate zone limit (i.e., bradycardia, normal, low rate VT, high rate VT, and fibrillation rate zones) and various other characteristics (e.g., sudden onset, stability, physiologic sensors, and morphology, etc.) in order to determine the type of remedial therapy that is needed (e.g., bradycardia pacing, anti-tachycardia pacing, cardioversion shocks or defibrillation shocks, collectively referred to as "tiered therapy").

Cardiac signals are also applied to the inputs of an analog-to-digital (A/D) data acquisition system 90. The data acquisition system 90 is configured to acquire intracardiac electrogram signals, convert the raw analog data into a digital signal, and store the digital signals for later processing and/or telemetric transmission to an external device 102. The data acquisition system 90 is coupled to the right atrial lead 20, and the right ventricular lead 30 through a switching and signal conditioning circuit 98 of the switch 74 to sample cardiac signals with any one or more of the electrodes of the right atrial lead 20 and right ventricular lead 30. The circuit 98 will be described more fully herein with reference to FIG. 3.

The microcontroller 60 is further coupled to a memory 94 by a suitable data/address bus 96, wherein the programmable operating parameters used by the microcontroller 60 are stored and modified, as required, in order to customize the operation of the stimulation device 10 to suit the needs of a particular patient. Such operating parameters define, for example, pacing pulse amplitude, pulse duration, electrode polarity, rate, sensitivity, automatic features, arrhythmia detection criteria, and the amplitude, waveshape and vector of each shocking pulse to be delivered to the patient's heart 12 within each respective tier of therapy. A feature of the present invention is the ability to sense and store data from the acquisition system 90, which data may then be used for subsequent analysis by an attending physician.

Advantageously, the operating parameters of the implantable device 10 may be non-invasively programmed into the memory 94 through a telemetry circuit 100 in telemetric communication with the external device 102, such as a programmer, transtelephonic transceiver, or a diagnostic system analyzer. The telemetry circuit 100 is activated by the microcontroller by a control signal 106. The telemetry circuit 100 advantageously allows intracardiac electrograms and status information relating to the operation of the device 10 (as contained in the microcontroller 60 or memory 94) to be sent to the external device 102 through an established communication link 104. The communication link 104 is further utilized for conveying the IEGMs, either prestored or in real time to the external programmer 102 for display. The IEGMs may be processed by the device 10 in a manner to be described subsequently to provide an IEGM display having the appearance of a surface EKG. Alternatively, conventional IEGM signals may be conveyed to the programmer 102 for processing, as also will be described subsequently, to provide an IEGM display having the appearance of a surface EKG.

The stimulation device 10 may further include a physiologic sensor 108, commonly referred to as a "rate-responsive" sensor because it is typically used to adjust pacing stimulation rate according to the exercise state of the patient. However, the physiological sensor 108 may further be used to detect changes in cardiac output, changes in the physiological condition of the heart, or diurnal changes in activity (e.g., detecting sleep and wake states). Accordingly, the microcontroller 60 responds by adjusting the various pacing parameters (such as rate, AV Delay, V-V Delay, etc.) at which the atrial and ventricular pulse generators, 70 and 72, generate stimulation pulses.

The stimulation device additionally includes a battery 110 which provides operating power to all of the circuits shown in FIG. 2. For the stimulation device 10, which employs shocking therapy, the battery 110 must be capable of operating at low current drains for long periods of time, and then be capable of providing high-current pulses (for capacitor charging) when the patient requires a shock pulse. The battery 110 must also have a predictable discharge characteristic so that elective replacement time can be detected. Accordingly, the device 10 preferably employs lithium/silver vanadium oxide batteries.

The stimulation device 10 further includes a magnet detection circuitry (not shown), coupled to the microcontroller 60. The purpose of the magnet detection circuitry to detect when a magnet is placed over the stimulation device 10, which magnet may be used by a clinician to perform various test functions of the stimulation device 10 and/or to signal the microcontroller 60 that the external programmer 102 is in place to receive or transmit data to the microcontroller 60 through the telemetry circuits 100.

As further shown in FIG. 2, the device 10 is shown as having an impedance measuring circuit 112 which is enabled by the microcontroller 60 via a control signal 114. The impedance measuring circuit 112 is not critical to the present invention and is shown for only completeness.

In the case where the stimulation device 10 is intended to operate as an implantable cardioverter/defibrillator (ICD) device, it must detect the occurrence of an arrhythmia, and automatically apply an appropriate electrical shock therapy to the heart aimed at terminating the detected arrhythmia. To this end, the microcontroller 60 further controls a shocking circuit 116 by way of a control signal 118. The shocking circuit 116 generates shocking pulses of low (up to 0.5 joules), moderate (0.5-10 joules), or high energy (11 to 40 Joules), as controlled by the microcontroller 60. Such shocking pulses are applied to the patient's heart 12 through at least two shocking electrodes, and as shown in this embodiment, selected from the left atrial coil electrode 28, the RV coil electrode 36, and/or the SVC coil electrode 38. As noted above, the housing 40 may act as an active electrode in combination with the RV electrode 36, or as part of a split electrical vector using the SVC coil electrode 38 or the left atrial coil electrode 28 (i.e., using the RV electrode as a common electrode).

Cardioversion shocks are generally considered to be of low to moderate energy level (so as to minimize pain felt by the patient), and/or synchronized with an R-wave and/or pertaining to the treatment of tachycardia. Defibrillation shocks are generally of moderate to high energy level (i.e., corresponding to thresholds in the range of 5-40 joules), delivered asynchronously (since R-waves may be too disorganized), and pertaining exclusively to the treatment of fibrillation. Accordingly, the microcontroller 60 is capable of controlling the synchronous or asynchronous delivery of the shocking pulses.

Figure 3:
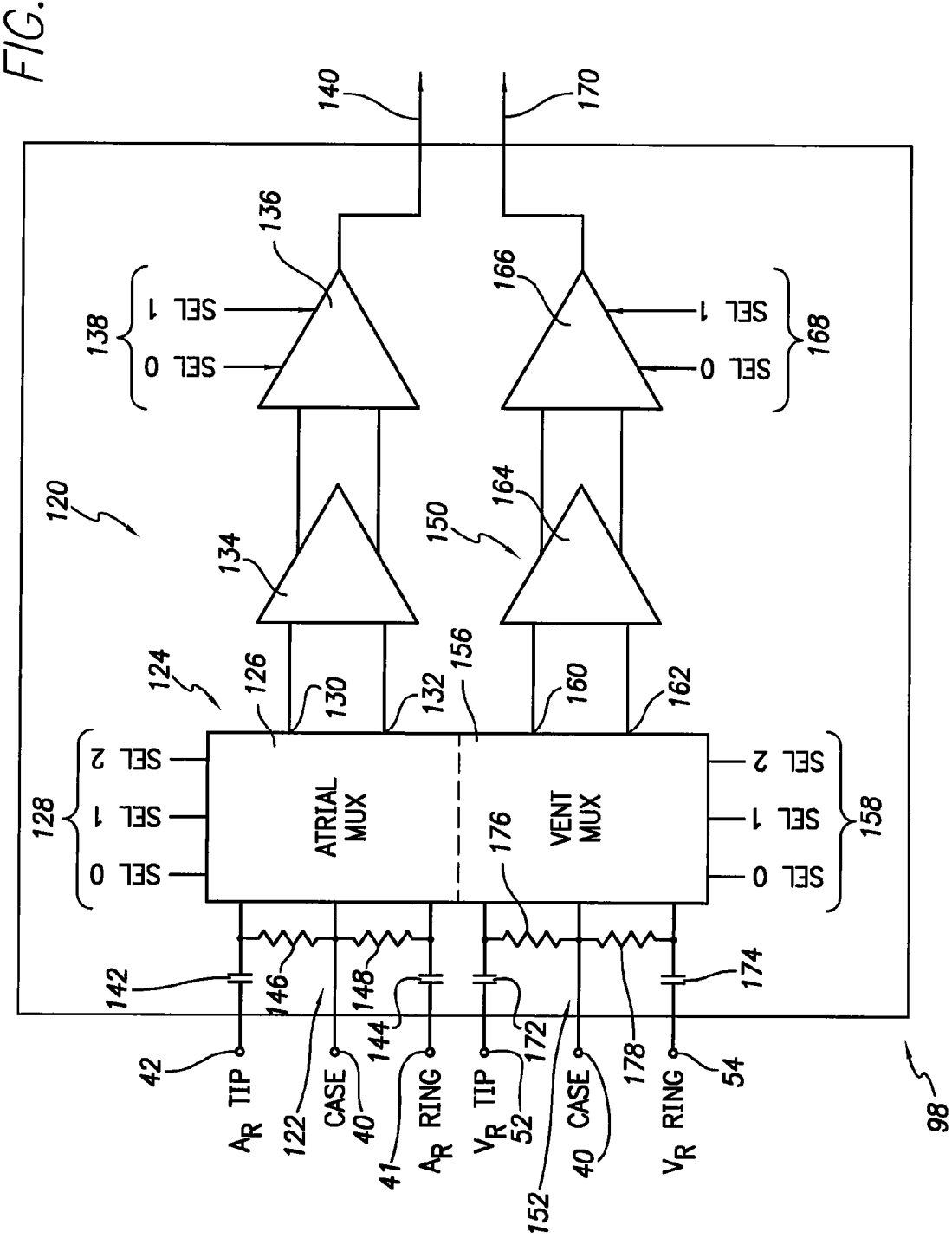
FIG. 3 is a schematic diagram of a circuit which provides high pass filtering of IEGMs within the device of FIGS. 1 and 2 to provide heart activity signals or IEGMs to be processed or to provide at least one heart activity signal for display which resembles a surface EKG.

Referring now to FIG. 3, it illustrates a schematic circuit diagram of the switching and signal conditioning circuit 98 of FIG. 2. The circuit 98 provides an atrial based IEGM channel 120 and a ventricular based IEGM channel 150. The channel 120 includes a high pace filter 122 and the channel 150 includes a high pass filter 152. The inputs of the high pass filter 122 are coupled to the right atrial tip terminal 42, the right atrial ring terminal 41 and the case terminal 40. In a similar manner, the inputs of the high pass filter 152 is coupled to the right ventricular tip terminal 52, the right ventricular ring terminal 54, and the case terminal 40.

The outputs of the high pass filter 122 are coupled to atrial section 126 of a multiplexer 124 and the outputs of the high pass filter 152 are coupled to the ventricular section 156 of the multiplexer 124.

A first group 128 of select lines enable the selected coupling of any of the filter output combinations to the outputs 130 and 132 of the multiplexer section 126 which are inputs to an atrial channel preamplifier 134. The various switch selection combinations are illustrated in FIG. 4. For example, if all select lines (Sel 0, Sel 1, Sel 2) of group 128 are made logical zeros, a filtered IEGM signal sensed from the right atrial tip electrode 22 to the right ventricular ring electrode 34 will be provided at the outputs 130 and 132 of the multiplexer section 126 for input into the amplifier 134. The other possible electrode configurations are shown in FIG. 4 to provide an IEGM signal from the right atrial tip electrode 22 to the case 40, the right atrial tip electrode 22 to the right ventricular ring electrode 34, the right atrial tip electrode 22 to the right atrial ring electrode 21, the right atrial ring electrode 21 to the right ventricular ring electrode 34, the right atrial ring electrode 21 to the case 40, the right atrial ring electrode 21 to the right ventricular tip electrode 32, and the right atrial ring electrode 21 to the right atrial ring electrode 21. Any one of the foregoing sensing electrode configurations may be utilized for providing an atrial based IEGM signal which, when displayed, will have an appearance of a surface EKG in accordance with the present invention.

Similarly, a second group 158 of select lines enable the selected coupling of any of the filter output combinations to the outputs 160 and 162 of the multiplexer section 156 which make inputs to a ventricular channel preamplifier 164. The various switch selection combinations are illustrated in FIG. 5. For example, if all select lines (Sel 0, Sel 1, Sel 2) of group 158 are made logical zeros, a filtered IEGM signal sensed from the right ventricular tip electrode 32 to the right atrial ring electrode 21 will be provided at the outputs 160 and 162 of the multiplexer section 156 for input into the amplifier 164. The other possible electrode configurations are shown in FIG. 5 to provide a ventricular based IEGM signal from the right ventricular tip electrode 32 to the case 40, the right ventricular tip electrode 32 to the right atrial ring electrode 21, the right ventricular tip electrode 32 to the right ventricular ring electrode 34, the right ventricular ring electrode 34 to the right atrial ring electrode 21, the right ventricular ring electrode 34 to the case 40, the right ventricular ring electrode 34 to the right atrial tip electrode 22, and the right ventricular ring electrode 34 to the right ventricular ring electrode 34. Any one of the foregoing sensing electrode configurations may be utilized to provide a ventricular based IEGM signal which, when displayed, has the appearance of a surface EKG in accordance with the present invention. As may also be appreciated by those skilled in the art, a still further sensing electrode configuration could include the right ventricular coil electrode 36.

The preamplifiers 134 and 164 preferably provide the IEGMs with a high frequency cutoff or roll-off of about 250 MHz as is conventional and make input to amplifiers 136 and 166 respectively. Each of the amplifiers is a dual to single ended amplifier with programmable gain by way of select lines 138 and 168 respectively. Such amplifiers are well known in the art. The outputs 140 and 170 respectively of amplifiers 136 and 166 are coupled to the inputs of the analog to digital acquisition system 90 of FIG. 2 which has a multiplexed output 91 to provide alternate eight bit data streams of the atrial and ventricular based filtered IEGMs.

Figure 9:
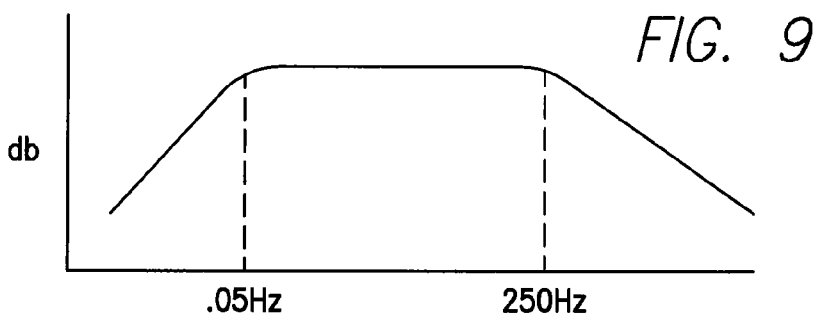
FIG. 9 is a graph illustrating the frequency characteristics of a processed IEGM which, when displayed, resembles a surface EKG.

If the sensed IEGMs are to be processed within the implanted device to provide one or both IEGMs having an appearance of a surface EKG, the component values of the high pass filters 122 and 152 are selected to provide a low frequency cutoff or roll-on no greater than 0.2 Hz while the preamplifiers 134 and 136 establish a high frequency cutoff or roll-off of no less than 20 Hz. As will be noted in FIG. 3, the high pass filter 122 includes capacitors 142 and 144 and resistors 146 and 148. Similarly, the high pass filter 152 includes capacitors 172 and 174 and resistors 176 and 178. By providing the capacitors 142, 144, 172, and 174 with a value of 0.66 MF and resistors 146, 148, 176 and 178 with a value of 5 megaohms, the IEGMs will be filtered with a roll-on frequency of about 0.05 Hz and a roll-off frequency of about 250 Hz to provide IEGMs having the appearance of a surface EKG. The frequency characteristics thus obtained are illustrated in FIG. 9. Of course, as one of ordinary skill would appreciate, the foregoing set of component values is only one example of the many different combinations of component values which may be used in practicing the present invention.

On the other hand, if the IEGM signals are to be processed within the external programmer or display, the capacitors 142, 144, 172, and 174 and resistors 146, 148, 176, and 178 may have more conventional values. Here, for example, the resistors 146, 148, 176, and 178 may again have values of 5 megaohms and the capacitors 142, 144, 172, and 174 may have values of 0.033 MF. These component values together with the conventional cutoff frequencies provided by amplifiers 134 and 164 provide more conventional filtering as may be seen in the filter characteristic illustrated in FIG. 7. Here, the roll-on frequency is on the order of 2 to 3 Hz and the roll-off frequency is on the order of 250 Hz. The more conventional IEGMs to be processed by the programmer or external display in accordance with the present invention may be processed by a programmer or external display as generally illustrated in FIG. 6.

Figure 6:
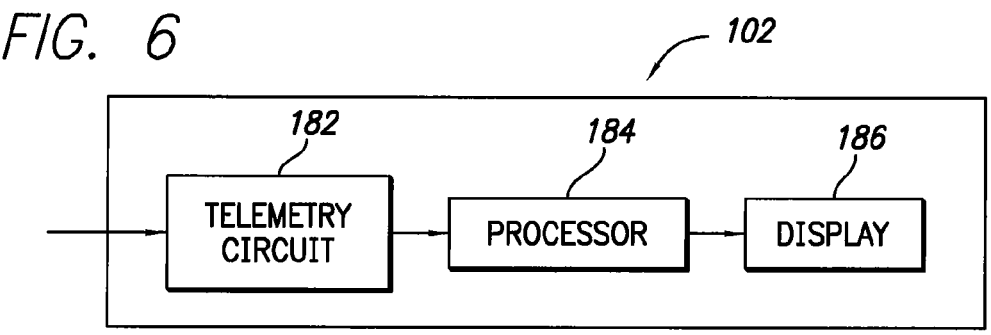
FIG. 6 is a simplified block diagram of the elements required in an external programmer for processing an IEGM and displaying the processed IEGM resembling a surface EKG.

The external programmer 102 of FIG. 6 includes a telemetry circuit 182, a processor 184, and a display 186. The telemetry circuit receives the IEGM data from the implanted device 10. The processor processes the received IEGMs by implementing a digital equalizing filter which may comprise two stages as will be described hereinafter with respect to FIG. 8. Once processed, the filtered IEGMs may be displayed on display 186 with an appearance of surface EKGS. Although not illustrated in FIG. 6, a printer may further be coupled to the processor 184 for making a hard copy of the filtered IEGMs in a conventional manner.

Figure 8:
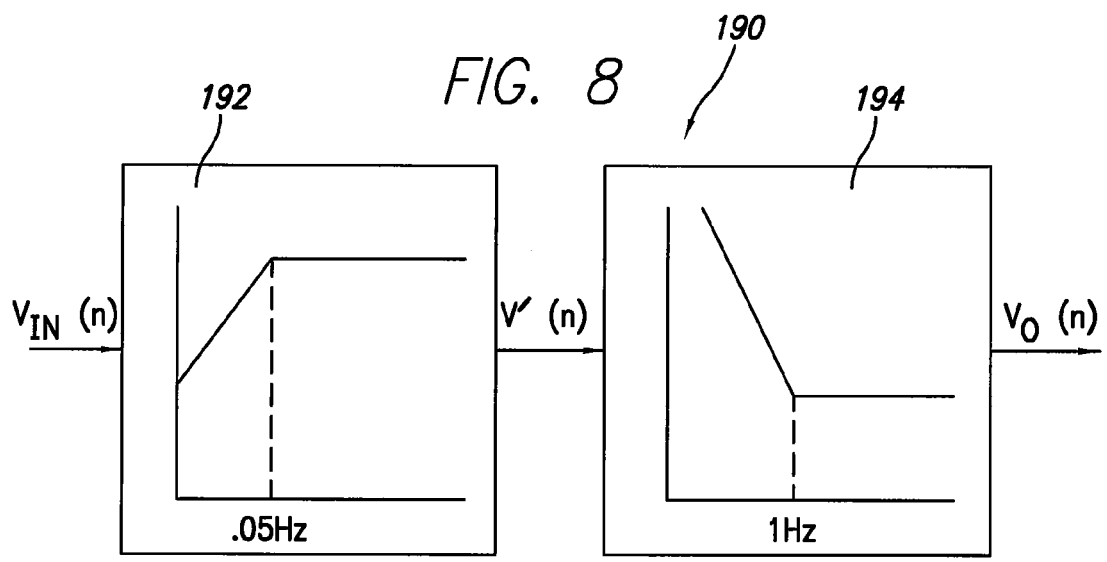
FIG. 8 is a block diagram illustrating the filtering stages of a digital filter which may be implemented by the processor of FIG. 6.

FIG. 8 shows the digital filter characteristics implemented by the processor 184 to filter the conventional IEGMs for providing IEGMs, which when displayed, have the appearance of surface EKGs. The digital filter 190 includes a first stage 192 and a second stage 194. The first stage 192 is a high pass filter with a low end cutoff of 0.05 Hz. The second stage 194 boosts the low frequencies in order to reestablish the low frequency content of the IEGMs previously lost because of the limited bandwidth available in the implanted device 10.

The first stage 192 characteristic may be represented by the equation below in a manner which may be appreciated by those skilled in the art.

Digital Filter for 0.05 Hz High Pass $$V'(n) = V'(n-1) + V_{in}(n) - V_{in}(n-1)$$

$$\left(1 + 2\pi \frac{f_L}{f_S}\right)$$

where $f_L$=0.05 Hz and $f_s$=Sampling Rate=512 samples/second with the initial condition that $V'(n-1)=V_{in}(n-1)$ furthermore $V_{in}(n)$ should be approximately a Zero mean signal to minimize settling.

11=1, 2, 3 to the final sample

The second stage 194 characteristic may be represented by the equation below, also in a manner which may be appreciated by those skilled in the art.

Figure 7:
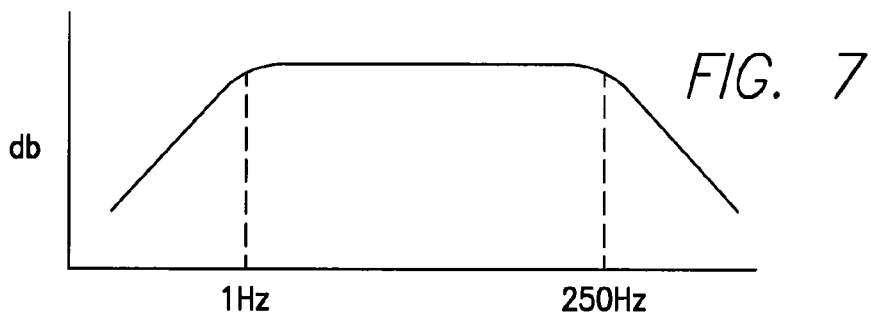
FIG. 7 is a graph illustrating the frequency characteristics of a conventional IEGM signal.

Digital Filter For Equalizer To Reestablish Low Frequencies $$V_o(n) = V_o(n-1) - V'(n-1) + \left(1 + 2\pi \frac{f_{eq}}{f_S}\right) V'(n)$$

where $f_{eq}$=1 Hz and $f_s$=Sampling Rate=512 samples/second with the initial condition that $V_o(n-1)=V_o'(n-1)$ n=1, 2, 3 to the final sample After the filter 190 implemented by the processor 184 acts upon the IEGM data received from the implanted device and having the frequency characteristics shown in FIG. 7, the filtered IEGMs to be displayed will have frequency characteristics as shown in FIG. 9. Here it may be observed that the filtered IEGMs will have a low frequency roll-on of 0.05 Hz and a high frequency roll-off of about 250 Hz. The displayed IEGMs will then have the appearance of a surface EKG.

FIG. 2 also show a filter/equalizer 62 which may be implemented by the microcontroller 60. The filter/equalizer may be the filter 190 of FIG. 8 or the other filters to be described hereinafter. The filters are, of course, implemented through digital signal processing. They restore to IEGMs low frequency information attenuated by high pass filters typically present at the front end of the signal chain in pacemakers and ICDs.

This is particularly useful in restoring diagnostic EKG-like morphology to ST segments and the T-waves. Parameters of the ST segment and the T-wave may be measured for the purpose of myocardial ischemia detection and for other purposes. This arrangement has the advantage that it may be efficiently implemented in the microcontroller firmware of a pacemaker or ICD requiring only shift and add operations.

Figure 10:
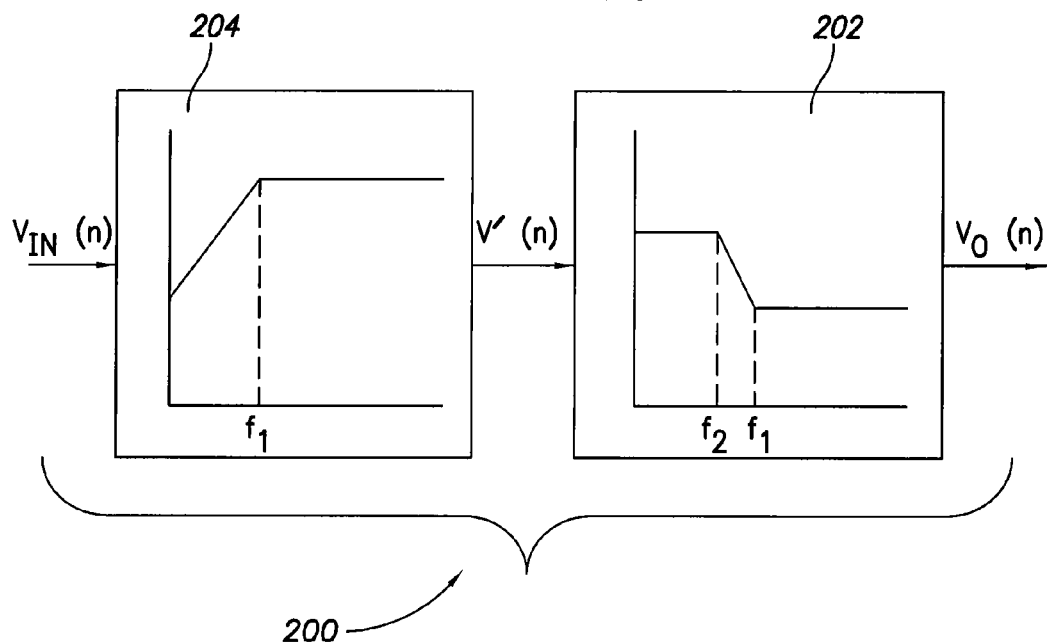
FIG. 10 is a block diagram illustrating the filtering stages of a further digital filter which may be implemented by the filter/equalizer of FIG. 2.

The frequency domain transfer function of a further filter/equalizer 200 according to the invention is shown in FIG. 10. The filter/equalizer 200 is characterized by an overall transfer function (FIG. 11) that may be derived from the transfer functions of an equalizer 202 and a high-pass filter 204. For example, the transfer function of the equalizer 202 may be the reciprocal transfer function of a high pass filter 204 with cutoff frequency (f1) at an upper frequency breakpoint, times the transfer function of a high pass filter with cutoff frequency (f2) at a lower frequency breakpoint. Its purpose is to boost low frequency amplitudes which are attenuated by the high-pass filter 204, which may be the front-end filters of pacemakers or ICDs. The low frequency amplitudes are boosted in order to restore slow-changing electrogram features such as the QT segment. The upper frequency breakpoint f1 of the equalizer 202 may be, for example, 1 Hz, while the lower frequency breakpoint f2 is preferably below 0.25 Hz, such as, for example, 0.05 Hz. It may be noted that the transfer function of the equalizer 202 flattens out below f2. This serves to minimize the gain at DC. In general terms, the transfer function of the equalizer is non-decreasing for frequencies up to the lower frequency breakpoint, decreasing for frequencies between the lower frequency breakpoint and the upper frequency breakpoint, and generally flat for frequencies above the upper frequency breakpoint through a bandpass region of interest.

It is also desirable to minimize the gain for frequencies which can contain no information, which is the case for frequencies below approximately f2. For example, assume the IEGM channel gain is set such that a signal uses the full dynamic range of the IEGM channel (8 bits yields approximately 48 dB of dynamic range). Also assume a $2^{nd}$ order response (40 dB/decade of frequency) of the pacer/ICD front end filter. Then frequency components of the signal at or below about 0.1 Hz have less than 1 bit resolution, i.e. they are lost in quantization noise. Any gain below 0.1 Hz then, can only boost noise.

Where:

f1=upper frequency breakpoint=1 Hz f2=lower frequency breakpoint=0.2 Hz $1^{st}$ Order Response The frequency domain transfer function for a $1^{st}$ order equalizer 202 is:

$$H_{j\omega} = \left(\frac{1}{HPF_1}\right)(HPF_2)$$

$$H_{j\omega} = \left(\frac{1+j\frac{\omega}{\omega_1}}{j\frac{\omega}{\omega_1}}\right)\left(\frac{j\frac{\omega}{\omega_2}}{1+j\frac{\omega}{\omega_2}}\right) = \frac{\omega_1 + j\omega}{\omega_2 + j\omega}$$

Where:

$\omega1=2\pi f1$ $\omega2=2\pi f2$ $2^{nd}$ Order Response

The high pass filter 204 at the front end of many pacemakers and ICDs is second order. It comprises two first-order high pass filters in series. The slope of the transfer function below f1 is 40 dB per decade. Therefore, the equalizer 202 preferably should also have a second-order response, i.e. the slope of the transfer function between f2 and f1 must be −40 dB per decade. The frequency domain transfer function for a $2^{nd}$ order equalizer is:

$$H_{j\omega} = \frac{\omega_1^2 + 2j\omega\omega_1 - \omega^2}{\omega_2^2 + 2j\omega\omega_2 - \omega^2}$$

Difference Equation

To achieve a $2^{nd}$ order response, the digitized signal may be filtered twice by the same equalizer of the type described herein or by serial equalizers, each being of the type described herein. This process is defined by the equation below.

$(1+k2)Vo(n)=Vi(n)+(k1)Vi(n)-Vi(n-1)+Vo(n-1)$

Where, ideally:

$\Delta T=1/$sample rate, e.g. $1/128=7.8125$ ms $k1=\omega1\Delta T=2\pi/128$ and $k2=\omega2\Delta T=2\pi/640$.

The answer, (1+k2)Vo, is a scaled version of the real answer Vo. Operations can be done directly on the scaled version. Alternately, Vo can be calculated or approximated. A second-order difference equation which achieves a $2^{nd}$ order response in a single pass may also be realized. However a $1^{st}$ order difference equation applied in two passes shall be hereinafter assumed for the sake of simplicity.

Implementation for Device Microcontroller Firmware

The difference equation of the 1 st order equalizer 202 may be adapted for a fixed-point implementation which uses only shift and add operations. This implementation is particularly suited to microcontroller firmware. These operations may be carried out using at least 2-byte signed arithmetic, assuming 8 bit resolution of Vi.

The first step is to approximate the coefficients k1 and k2 with numbers which are powers of two. This will facilitate divide and multiply operations which may be accomplished by right and left shift operations, respectively. Therefore:

let $k1=1/16\sim2\pi/128$ and let $k2=1/128\sim2\pi/640$.

Difference Equation:

$(1+k2)Vo(n)=Vi(n)=(k1)Vi(n)-Vi(n-1)+Vo(n-1)$ $(1+\frac{1}{128})Vo(n)=Vi(n)+(\frac{1}{32})Vi(n)-Vi(n-1)+Vo(n-1)$ Multiply through by 256:

$(256+2)Vo(n)=(256)Vi(n)+(8)Vi(n)-(256)Vi(n-1)+(256)Vo(n-1)$

Multiplication by 256 may be accomplished by moving the least significant(LS) byte to the most significant (MS) byte position. Multiplication by 8 may be accomplished by left-shifting 3 bits, etc.

It is necessary to calculate or approximate 256Vo(n−1) given 258Vo(n−1) in order to provide the last term in the difference equation.

256Vo can be approximated as follows:

$256Vo \sim 258Vo - 2*258Vo/256$ where division of 258Vo by 256 may be performed by moving the MS byte of 258Vo to the LS byte position.

The answer 258Vo is a scaled version of the real answer Vo. Operations can be done directly on the scaled version, or Vo can be calculated or approximated. Vo can be approximated by simply throwing away the low byte and keeping the high byte, equivalent to dividing by 256. Again, the 1st order process defined above applied to an electrogram segment in two passes produces the required 2nd order response.

It should be noted that, since there is non-zero gain at DC in the equalizer transfer function, the average value of any signal processed by this equation must be zero. Otherwise the Vo will rise with time towards a level equal to the average value of the signal times the equalizer gain at DC. Therefore, IEGM data typically represented in devices using 256 unsigned integer values (from 0 to 255 with 128 being the average baseline "0" value) should be converted to signed integers before processing, with zero average value over the set of samples to be processed.

Figure 11:
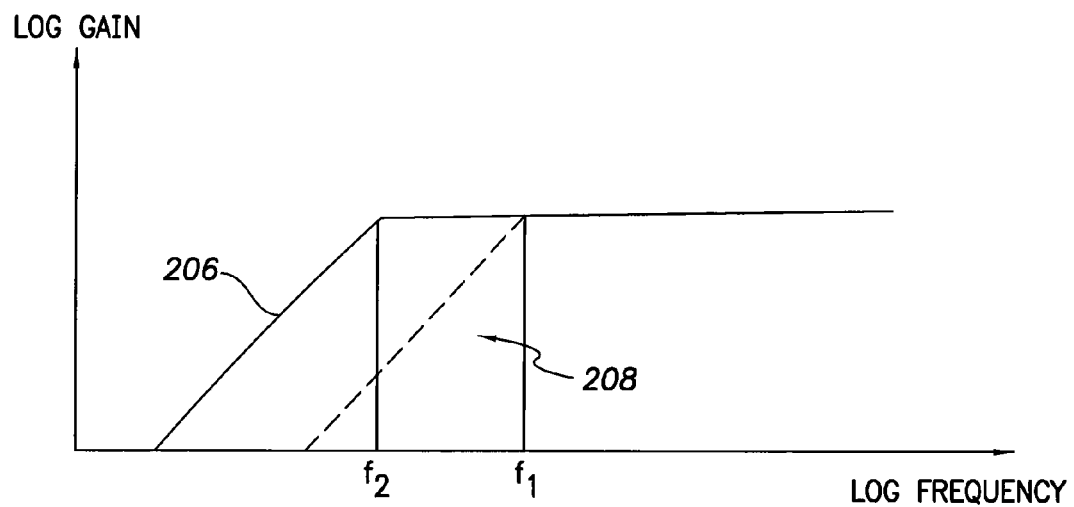
FIG. 11 is a graph illustrating the low frequency characteristics of a processed IEGM, a conventional IMD IEGM, and the overall transfer function of the filter of FIG. 10.

FIG. 11 shows the resulting overall transfer function 206 at low frequencies when the filter 200 of FIG. 10 is implemented as described above. It may be noted that the resulting overall transfer function 206 has a break point at frequency f2 while the original device transfer function 208, without the filter/equalizer 200, has a break point at frequency f1.

Figure 12:
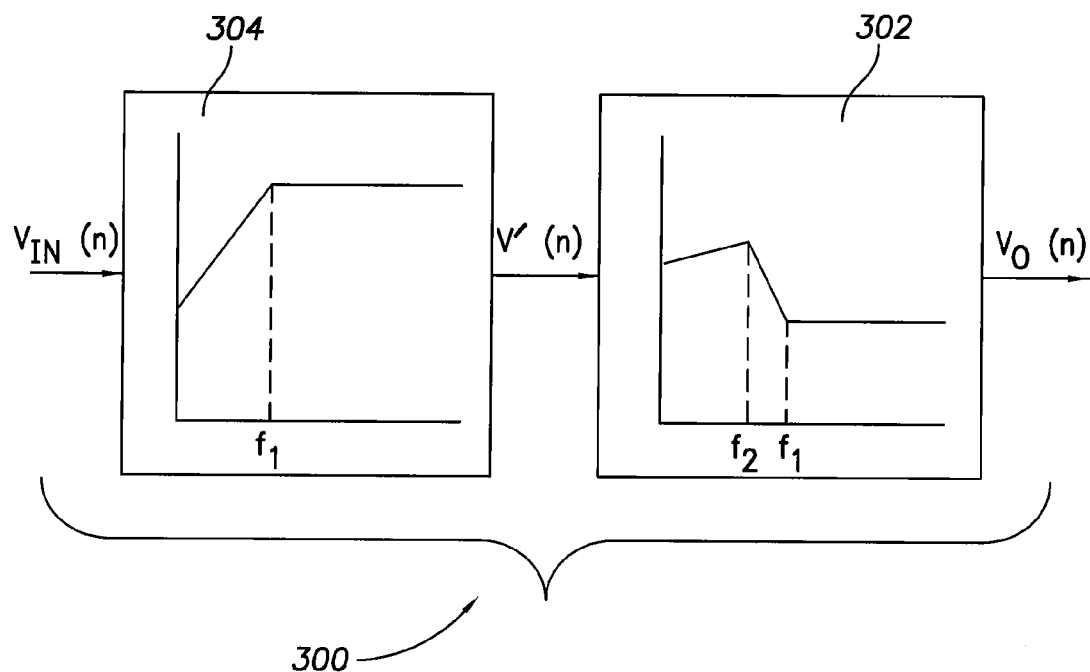
FIG. 12 is a block diagram illustrating the filtering stages of a still further digital filter which ma be implemented by the filter/equalizer of FIG. 2.

FIG. 12 illustrates a further filter/equalizer 300 according to the invention. Here it will be noted that the pacer or ICD filter 304 has a transfer function similar to that of the filter 204 of FIG. 10. The equalizer transfer function 302 is the same as the transfer function 202 except that, the transfer function 302 decreases for frequencies below frequency f2. This has the effects of eliminating the gain at DC for the equalizer stage and reducing the overall gain at frequencies below f2 where there is only noise and no information to be measured.

Figure 13:
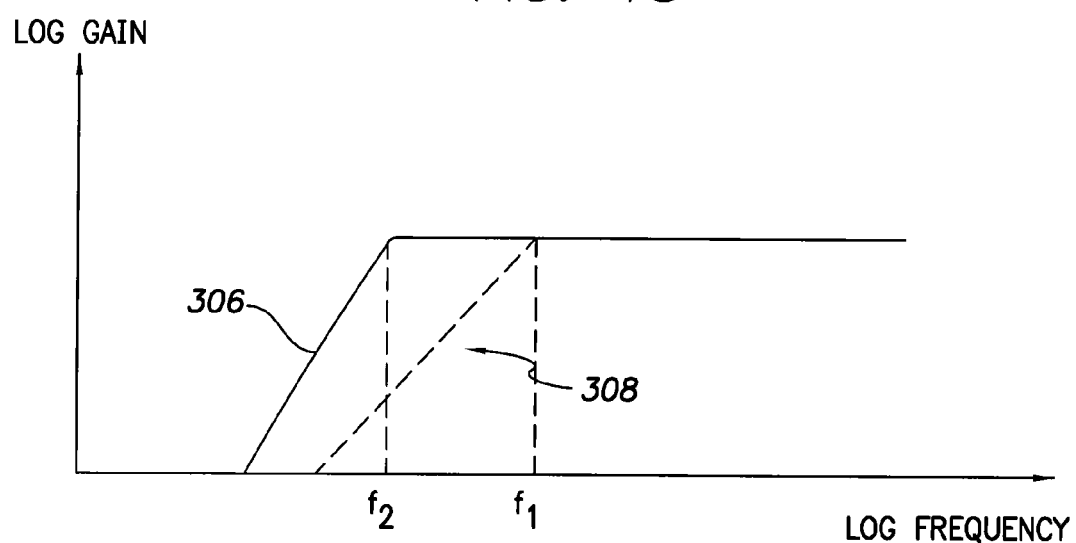
FIG. 13 is a graph illustrating the low frequency characteristics of a processed IEGM, a conventional IMD IEGM, and the overall transfer function of the filter of FIG. 12.

The foregoing results in the final overall transfer function 306 of FIG. 13 which may be compared to the original transfer function 308. The overall transfer function 306 is essentially identical to the overall transfer function 206 except that the transfer function 306 has a greater slope below frequency f2.

This may be accomplished by duplicating the HPF2 transfer function as shown below. The transfer function shown below also must be applied in two passes in order to achieve a 40 db/decade slope between f2 and f1.

$$H_{j\omega} = \left(\frac{1}{HPF_1}\right)(HPF_2)(HPF_2)$$

$$H_{j\omega} = \left(\frac{1+j\frac{\omega}{\omega_1}}{j\frac{\omega}{\omega_1}}\right)\left(\frac{j\frac{\omega}{\omega_2}}{1+j\frac{\omega}{\omega_2}}\right)\left(\frac{j\frac{\omega}{\omega_2}}{1+j\frac{\omega}{\omega_2}}\right)$$

According to further aspects of the invention, detection or monitoring of ischemia may be performed by measuring ST segment amplitudes measured from EGMs processed by the filter/equalizers previously described herein. Again, such ST segment amplitude measurements are rendered possible because the slowing changing EGM features are restored to the EGMs commonly generated within the implantable cardiac stimulation devices. Ischemia may be considered present if the ST segment amplitudes are elevated above a baseline by a certain factor. In accordance with the present invention, the baseline is the pre-P isoelectric baseline. To this end, the processed (filtered) EGMs may be prestored in memory before measurements are made. The EGM storing preferably commences at a time to assure that a period beginning about 50 ms before each P wave is captured. The pre-P isoelectric values may then be measured for each cardiac cycle along with its corresponding ST segment amplitude. Alternately, the isoelectric baseline may be taken in the P-R interval, e.g. about 50 mS before each R-wave.

Figure 14:
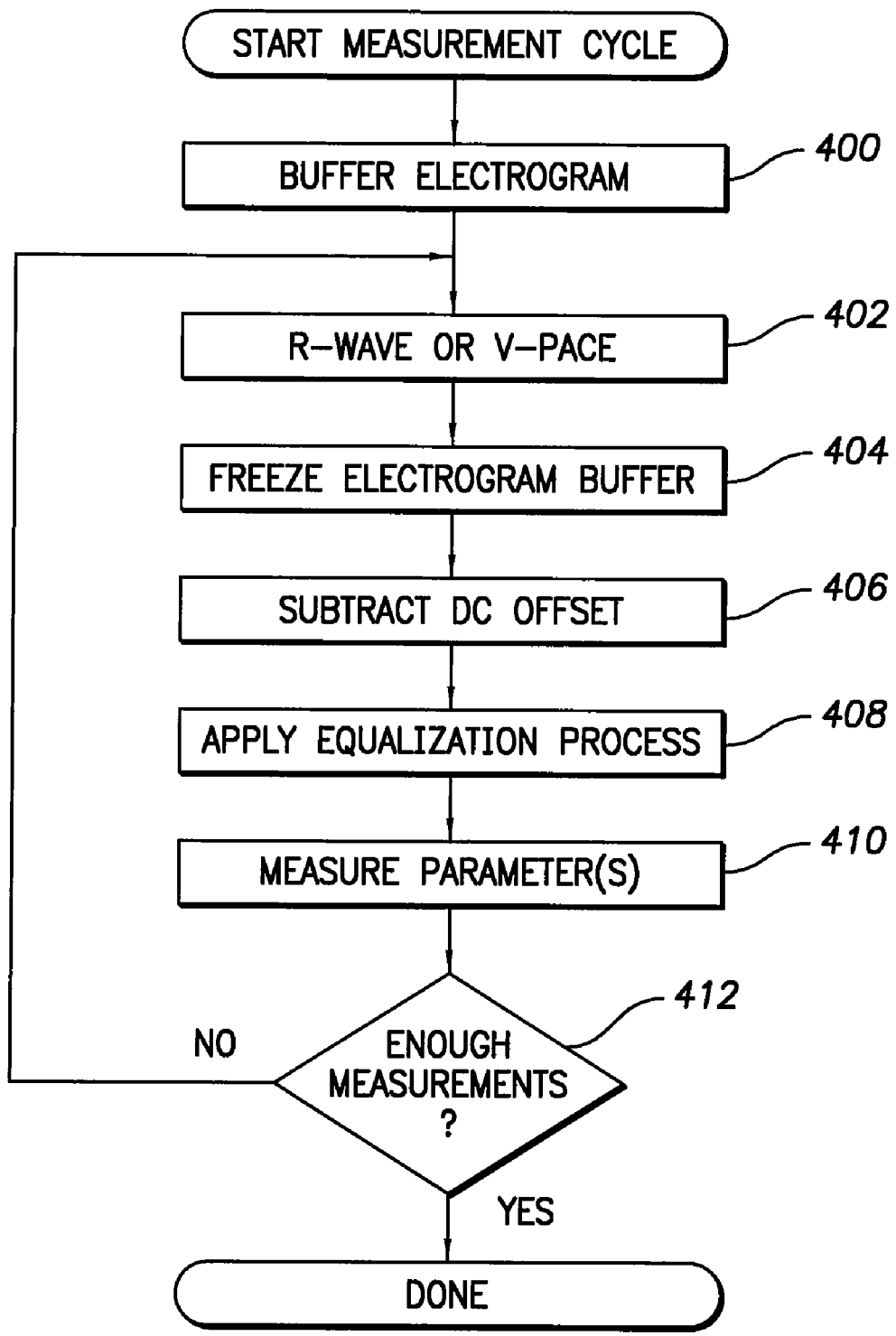
FIG. 14 is a flow chart describing the manner in which the microcontroller of FIG. 2 may collect ST segment data for ischemia detection according to one embodiment.

In FIG. 14, a flow chart is shown describing an overview of the operation and novel features implemented in one embodiment of the device 10. In this flow chart, and the flow chart of FIG. 15 described herein, the various algorithmic steps are summarized in individual "blocks". Such blocks describe specific actions or decisions that must be made or carried out as the algorithm proceeds. Where a microcontroller (or equivalent) is employed, the flow charts presented herein provide the basis for a "control program" that may be used by such a microcontroller (or equivalent) to effectuate the desired control of the stimulation device. Those skilled in the art may readily write such a control program based on the flow charts and other descriptions presented herein.

The process of FIG. 14 is directed to collecting ST segment data for ischemia monitoring or detection. The process initiates with activity block 400 wherein EGM storage is initiated. The EGMs stored in accordance with activity block 400 are the EGMs developed by the implantable cardiac stimulation device before being applied to an equalizer in accordance with the present invention. The process then advances to activity block 402 where it is determined, as the current cardiac cycle is being recorded, if the current cardiac cycle includes an intrinsic R wave or a paced ventricular event. This step is undertaken so that separate data is taken for cardiac cycles with intrinsic R waves and cardiac cycles with paced ventricular events. The process then advances to activity block 404 wherein after the EGM of the current cardiac cycle has been stored through at least the T wave, the memory is temporarily frozen. Next, in activity block 406, a DC offset is subtracted from each of the stored EGM values. More specifically, the average value of the buffered EGM segment (e.g. 50 milliseconds pre-P through the end of the T-wave) to be zero. This may be implemented by calculating the average value of the entire signal in memory and subtracting that value from each sample. Note that the time for calculating the average may be reduced if the number of samples in the buffered segment is a power of two. Then after summing the value of the buffered samples division can be effected by a shift operation. Next, in step 408, the stored electrogram is filtered or equalized. The stored electrogram or electrogram segment may be equalized as previously described by digitally filtering the stored EGM with any one of the digital equalizers described herein. As previously mentioned, if a second order response is required, the stored EGMs are preferably applied twice to the equalizers. Upon completion of activity block 408, the electrogram will have its low frequency response restored to enable measurement of slowly changing features therein.

The process then advances to activity block 410 wherein the required parameters are measured. For ischemia monitoring, as contemplated herein, ST segment amplitudes are measured. However, other slowly changing electrogram features may also be measured such as T-wave morphology for monitoring blood glucose levels or cardioactive drug action or P-R segment elevation. Next, in decision block 412, it is determined if enough measurements have been taken. If not, the process returns to activity block 402. If enough measurements have been taken, it will have been determined that enough data exists to detect the presence or absence of ischemia, for example. Typically, four to 10 measurements are expected to be enough. It is expected that processing steps 402-412 may take several seconds or minutes. Therefore, it is likely that parameters will not be measured for consecutive cardiac cycles. Also, at step 410, it is contemplated that the measurements be stored. If both sensed and paced complexes have been measured, sensed and paced measurements are stored separately.

Figure 15:
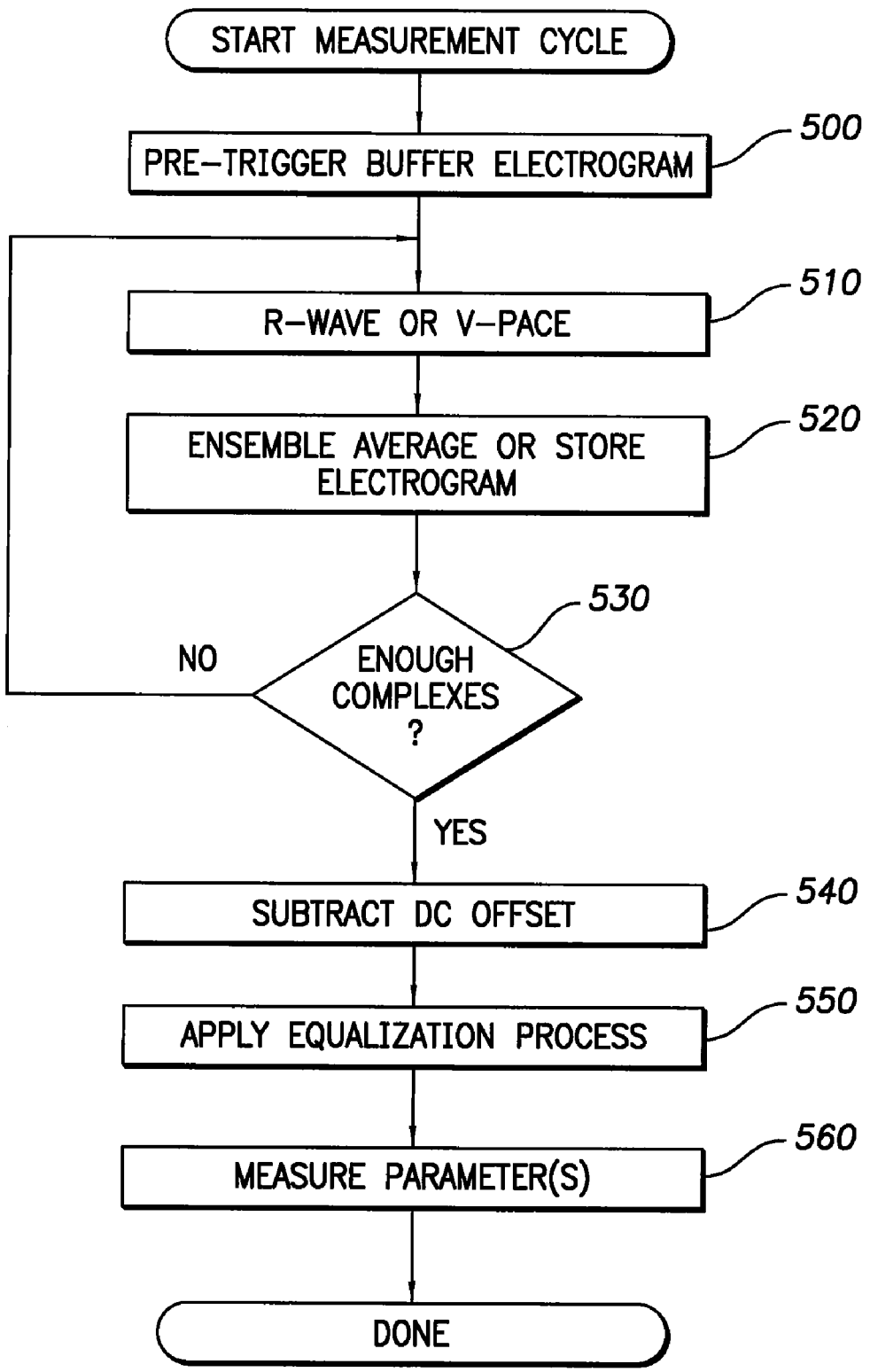
FIG. 15 is a flow chart describing another process in which the microcontroller of FIG. 2 may collect ST segment data for ischemia detection.

FIG. 15 describes another process in which the microcontroller 60 of FIG. 2 may collect ST segment data for ischemia monitoring or detection. The process initiates with activity block 500 wherein EGM storage is commenced as previously described. Next, in activity block 510, it is determined if the current cardiac cycle includes an intrinsic R wave or a paced ventricular event. The process then advances to 520 wherein the EGM of the current cardiac cycle is stored in an ensemble of previously stored EGMs. Also, the ensembles stored during activity block 520 may represent an ensemble average of several successive electrogram complexes. Ensemble averaging may be performed as follows:

$$Y * V\text{newavg}(n) = X * Vi(n) + (Y-X) * V\text{oldavg}(n)$$

For each sample n in the electrogram segments. Voldavg is the ensemble averaged segment from the previous pass. Vnewavg replaces Voldavg after the newly acquired segment is averaged in. Vi is a newly acquired segment. Exemplary values of X and Y may be 1 and 8, respectively. The above method avoids division which may be computationally costly, and which may result in significant loss of precision in the case of integer division. Ensemble averaging, especially by the preferred method described herein, also increased the effective signal-to-noise ratio for low-frequency components, thus improving the results of the equalization process. Whether segments are stored individually or ensembled averaged together, sensed and paced segments are processed separately.

The process then advances to decision block 530 where it is determined if enough complexes have been captured. If not, the process returns to activity block 510. If enough complexes have been captured, the process then advances to activity block 540 wherein the DC offset is subtracted from the sampled values as previously described. Next, in activity block 550 the ensemble averaged segment is applied to any one of the digital equalizers described herein for restoring the slowly changing EGM features therein.

After the EGM has been digitally filtered or equalized, the process then advances to activity block 560 wherein the desired parameters, such as ST segment elevation, are measured. The results may be stored for later use. Also, as previously mentioned, paced and sensed measurements are preferably kept separate.

While the invention has been described by means of specific embodiments and applications thereof, it is understood that numerous modifications and variations could be made thereto by those skilled in the art without departing from the spirit and scope of the invention. It is therefore to be understood that within the scope of the claims, the invention may be practiced otherwise than as specifically described herein.

What is claimed is:

1. An implantable cardiac system including an implantable cardiac stimulation device, the system providing a heart activity signal of a heart facilitating measurement of slowly changing electrogram features, the system comprising:
   at least one implantable electrode arrangement that senses cardiac electrical activity and provides an intracardiac electrogram signal;
   a first high-pass filter with a cutoff frequency at an upper frequency breakpoint that filters the intracardiac electrogram signal, and
   an equalizer that filters the filtered intracardiac electrogram signal, the equalizer having a transfer function derived by multiplying a reciprocal of the transfer function of the first high pass filter by a transfer function of a second high pass filter with a cutoff frequency at a lower frequency breakpoint, wherein the transfer function of the equalizer is non-decreasing for frequencies up to the lower frequency breakpoint.

2. The system of claim 1 wherein the implantable cardiac stimulation device includes a memory that stores the intracardiac electrogram signal prior to being filtered.

3. The system of claim 1 wherein the transfer function of the equalizer increases for frequencies up to the lower frequency breakpoint.

4. The system of claim 1 wherein the transfer function of the equalizer has a second order response from the lower frequency breakpoint to the upper frequency breakpoint.

5. The system of claim 1 wherein the upper frequency breakpoint is on the order of 1 Hertz.

6. The system of claim 1 wherein the lower frequency breakpoint is less than about 0.25 Hertz.

7. The system of claim 1 wherein the at least one electrode arrangement comprises an electrode adapted for implant in the right atrium of the heart.

8. The system of claim 1 wherein the at least one electrode arrangement comprises an electrode adapted for implant in, on or proximate to a ventricle of the heart.

9. The system of claim 1 wherein the at least one electrode arrangement comprises a first electrode adapted for implant in, on or proximate to an atrium of the heart and a second electrode adapted for implant in, on or proximate to a ventricle of the heart.

10. In an implantable cardiac system, a method of providing a heart activity signal of a heart which facilitates measurement of slowly changing electrogram features, the method comprising:
    sensing cardiac electrical activity with at least one implanted electrode arrangement to provide an electrogram signal;
    filtering the electrogram signal with a first high-pass filter with a cutoff frequency at an upper frequency breakpoint; and filtering the filtered electrogram signal with a equalizer having a transfer function that is: non-decreasing for frequencies up to a lower frequency breakpoint that is less than the upper frequency breakpoint, decreasing for frequencies between the lower frequency breakpoint and the upper frequency breakpoint, and generally flat for frequencies above the upper frequency breakpoint through a bandpass region of interest.

11. The method of claim 10 wherein the transfer function of the equalizer increases for frequencies up to the lower frequency breakpoint.

12. The method of claim 10 wherein the transfer function of the equalizer has a second order response from the lower frequency breakpoint to the upper frequency breakpoint.

13. The method of claim 10 wherein filtering the filtered electrogram comprises twice filtering the intracardiac signal with the equalizer to obtain a second order response.

14. An implantable cardiac system including an implantable cardiac stimulation device, the system providing a heart activity signal of a heart facilitating measurement of slowly changing electrogram features, the system comprising:

at least one implantable electrode arrangement that senses cardiac electrical activity and provides an electrogram signal;

a first high-pass filter with a cutoff frequency at an upper frequency breakpoint that filters the electrogram signal, and a plurality of serially arranged equalizers that filter the filtered electrogram signal, each equalizer having a transfer function derived as a function of a reciprocal of the transfer function of the first high pass filter and a transfer function of a second high pass filter with a cutoff frequency at a lower frequency breakpoint.

15. The system of claim 14 wherein the transfer function of at least one of the equalizers is non-decreasing for frequencies up to the lower frequency breakpoint.

16. The system of claim 14 wherein the transfer function of at least one of the equalizers increases for frequencies up to the lower frequency breakpoint.

* * * * *